US009750673B2

(12) United States Patent
Chevet et al.

(10) Patent No.: US 9,750,673 B2
(45) Date of Patent: *Sep. 5, 2017

(54) COSMETIC COMPOSITION COMPRISING A BITTER COMPOUND, A FRAGRANCE, AN EXTRACT OF STEVIA AND A SALT

(75) Inventors: Karine Chevet, Chateauneuf sur Loire (FR); Valérie Alard, Orleans (FR); Eric Perrier, Les Cotes d'Arey (FR); Marie-Laure Souvie, Semoy (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/601,446

(22) Filed: Aug. 31, 2012

(65) Prior Publication Data

US 2013/0064782 A1    Mar. 14, 2013

(30) Foreign Application Priority Data

Sep. 9, 2011   (FR) ..................................... 11 58050

(51) Int. Cl.
| | | |
|---|---|---|
| *A61K 8/34* | (2006.01) | |
| *A61K 8/49* | (2006.01) | |
| *A61K 8/41* | (2006.01) | |
| *A61K 8/42* | (2006.01) | |
| *A61K 8/35* | (2006.01) | |
| *A61K 8/368* | (2006.01) | |
| *A61K 8/44* | (2006.01) | |
| *A61K 8/46* | (2006.01) | |
| *A61Q 1/14* | (2006.01) | |
| *A61K 8/60* | (2006.01) | |
| *A61K 8/64* | (2006.01) | |
| *A61K 8/97* | (2017.01) | |
| *A61Q 19/00* | (2006.01) | |
| *A61Q 17/04* | (2006.01) | |

(52) U.S. Cl.
CPC ............... *A61K 8/345* (2013.01); *A61K 8/35* (2013.01); *A61K 8/368* (2013.01); *A61K 8/41* (2013.01); *A61K 8/42* (2013.01); *A61K 8/442* (2013.01); *A61K 8/445* (2013.01); *A61K 8/447* (2013.01); *A61K 8/466* (2013.01); *A61K 8/49* (2013.01); *A61K 8/496* (2013.01); *A61K 8/498* (2013.01); *A61K 8/4946* (2013.01); *A61K 8/4953* (2013.01); *A61K 8/60* (2013.01); *A61K 8/602* (2013.01); *A61K 8/645* (2013.01); *A61K 8/97* (2013.01); *A61Q 1/14* (2013.01); *A61Q 19/00* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 2,463,264 A | 3/1949 | Graenacher et al. | |
| 5,585,091 A | 12/1996 | Pelzer et al. | |
| 7,473,707 B1 | 1/2009 | O'Lenick et al. | |
| 2005/0249689 A1 | 11/2005 | Kuo et al. | |
| 2007/0116835 A1 | 5/2007 | Prakash et al. | |
| 2007/0166336 A1 | 7/2007 | Delmarre et al. | |
| 2007/0224292 A1 | 9/2007 | Brunner et al. | |
| 2007/0292582 A1 | 12/2007 | Prakash et al. | |
| 2010/0178408 A1* | 7/2010 | Matuschek et al. | 426/534 |
| 2011/0085994 A1 | 4/2011 | Patel et al. | |
| 2011/0160311 A1* | 6/2011 | Prakash et al. | 514/777 |
| 2013/0064781 A1 | 3/2013 | Chevet et al. | |

FOREIGN PATENT DOCUMENTS

| | | |
|---|---|---|
| CN | 101559077 | 10/2009 |
| EP | 0669323 | 8/1995 |
| WO | WO2011/130705 | 10/2011 |

OTHER PUBLICATIONS

Mennella, J. A.; Pepino, M. Y.; Beauchamp, G. K. Modification of Bitter Taste in Children. Dev. Psychobiol. 2003, 43(2), 120-127.*
Anonymous "UV Spectroscopic Analysis of Caffeine & Benzoic Acid in Soft Drinks", URL: http://www.chm.uri.edu/sgeldart/chm_414/414%20Ultraviolet%20Spectroscopy.pdf, Feb. 2009.
Database WPI Week 200973, Thomson Scientific, London, GB; AN 2009-Q064968, Oct. 2009, XP002673562 (Chinese Application No. CN20091049420, published as No. CN101559077).
Database GNPD [Online] Mintel; Anonymous: "Sonnenmilch 2-30", Jul. 1999, XP002673556.
Database GNPD [Online] Mintel; Anonymous: "Exfoliating Body Gel", Dec. 2005, XP002673557.
Anonymous "Apple and Apple Phytochemicals, how strange a common fruit so magic use?", URL: http://www.mdidea.com/products/proper/proper00705.html, Dec. 2010, XP002673709.
Database GNPD [Online] Mintel; Anonymous "Conditioner with UV Filter", Jun. 2001, XP002673558.
Database GNPD [Online] Mintel; Anonymous "Cool Eye Color", Jun. 2007, XP002673559.
Database GNPD [Online] Mintel; Anonymous "Hot Body Lifting Gel", Jun. 2011, XP002673560.
Database GNPD [Online] Mintel; Anonymous "Lip Balm", Aug. 2008, XP002673710.
Database GNPD [Online] Mintel; Anonymous "Thermo Anti Cellulite Intensive Cure Creme Gel", Aug. 2009, XP002673711.
Anonymous "Evergreen Ivy Medicinal Action and Uses", URL: http://www.mdidea.com/products/proper/proper08305.html, Dec. 2010, XP002673712.
Database GNPD [Online] Mintel; Anonymous "Ginseng, Strawberry, Mint and Lemonade Drink", Feb. 2010, XP002673713.
V. Vummaneni et al.: "Taste Masking Technologies: An Overview and Recent Updates"; International Journal of Research in Pharmaceutical and Biomedical Sciences; 2012, vol. 3, pp. 510-524.

(Continued)

*Primary Examiner* — Jessica Worsham
(74) *Attorney, Agent, or Firm* — Hamre, Schumann, Mueller & Larson, P.C.

(57) ABSTRACT

The subject of the invention is the use of an extract of *Stevia* in combination with a salt, for masking the bitterness of bitter compounds in cosmetic or dermatological compositions.
This mixture of sweetener with a second gustatory agent makes it possible to mask the bitterness of the compound permanently without changing the nature of the fragrance or the colour of the composition.

13 Claims, No Drawings

(56) References Cited

OTHER PUBLICATIONS

Cilurzo et al.: "Diclofenac fast-dissolving film: suppression of bitterness by a taste-sensing system"; Drug Development and Industrial Pharmacy, 2011, vol. 37(3)pp. 252-259 (9 pages).

* cited by examiner

COSMETIC COMPOSITION COMPRISING A BITTER COMPOUND, A FRAGRANCE, AN EXTRACT OF STEVIA AND A SALT The invention relates to a cosmetic or dermatological composition intended to be applied to the facial skin, comprising at least one cosmetic ingredient with a bitter taste, an aqueous phase, a fragrance, at least one steviol glucoside and at least one salt.

PRIOR ART AND PURPOSES OF THE INVENTION

In order to apply a care cream, a liquid foundation or a sun cream to the face, the user generally takes a sufficient amount of cream in the hand in order to then spread it over the facial skin and to promote its penetration by rubbing. A generous application of the cosmetic product can result in the product unintentionally spilling over onto the lips.

It has, however, been observed that some of these care or makeup products for the face give a very bitter taste when they come into contact with the area around the lips during their application to the whole of the face, and it has been proposed, in document US 2011/0085994, to mask the bitterness of UVA and UVB sunscreens by incorporating a particular polyoxyalkylenated polyester into the cosmetic products. These products do not contain a fragrance.

As it happens, the inventors have demonstrated that certain products used for masking the bitterness of biologically active ingredients which are bitter in cosmetic compositions for the face, i) either are ineffective for masking the bitterness permanently, ii) or modify the odour of the composition, in particular when they contain a fragrance.

The main purpose of the invention is therefore to solve the technical problem consisting of the provision of a fragranced cosmetic or dermatological composition intended to be applied to facial skin, containing a bitter compound, the bitterness of which is masked at the moment of unexpected contact of the composition with the lips during the application of the product by the user. The masking of the bitterness of the bitter compound is prolonged over time and does not change the olfactory signature of the cosmetic or dermatological composition.

The Applicant has discovered, entirely unexpectedly, that it is possible to effectively mask the bitterness of a compound in a composition comprising a fragrance without changing the perception of the fragrance of the composition, by incorporating, in a sufficient amount, the combination of a steviol glucoside with a salt.

DESCRIPTION OF THE INVENTION

Thus, the subject of the present invention is a cosmetic or dermatological composition in the form of a facial care cream, of a face lotion, of a face serum or fluid, of a foundation, of a milk, of a makeup-removing lotion, or of a facial antisun product, comprising at least one organic ingredient with a bitter taste, an aqueous phase, a fragrance, at least one steviol glucoside as first gustatory agent, and at least one chloride salt as second gustatory agent chosen from sodium chloride, potassium chloride and zinc chloride, and mixtures thereof.

When the organic ingredient with a bitter taste is a sunscreen which screens out UVA or UVB rays, the composition preferably contains very low contents of ester of a fatty acid and of a polyoxyalkylenated polyol as described in document U.S. Pat. No. 7,473,707. This ester is obtained by reacting a glyceryl alkoxylate, a glycol alkoxylate or a sorbitol alkoxylate with a fatty acid comprising from 7 to 21 carbon atoms. The polyoxyalkylene polyol can be obtained beforehand by reacting the polyol with ethylene oxide and/or propylene oxide, and it generally contains from 1 to 5 oxyalkylene units. The ester may be sorbeth-2 hexaoleate. The weight ratio between the sunscreen and the ester is preferably less than 0.6. The composition is advantageously devoid of an ester salt.

According to the invention, the sensation of bitterness generated by the bitter compound at the moment it is applied to the lips is masked. With the combination of gustatory agents of the invention, it has been possible to obtain persistence of the masking of the bitterness of the compound for at least 10 minutes, or even for at least 15 minutes, after the accidental application of the composition to the lips. Surprisingly, the combination of the two gustatory agents allows persistent masking of the bitterness of the bitter ingredient, or even definitive masking of the bitterness of the bitter ingredient.

In the composition of the invention, the steviol glucoside and the chloride salt are advantageously present in the composition in an amount sufficient to mask the bitterness of the organic ingredient with a bitter taste, once the composition is applied to the lips or the area around the lips.

The composition according to the invention contains an organic ingredient which gives a sensation of bitterness once the composition is applied to the lips. The ingredient is preferably cosmetic or dermatological, more preferably an ingredient which has a biological activity.

Bitterness is a characteristic which is felt at the back of the tongue and of the palate. It can be evaluated by a panel of users who have previously been trained in the recognition and quantitative evaluation of the level of bitterness of a composition such that the evaluations of each user are reproducible, and that the average measurement of the bitterness of a product measured by this panel is reliable.

For the purpose of the invention, the expression "cosmetic or dermatological ingredient" is intended to mean an ingredient which is authorized for use pursuant to the regulations in force in the country in which the cosmetic or dermatological product which contains it is manufactured or marketed.

The bitterness of the ingredient can be evaluated by placing 0.2 g of an aqueous solution containing 0.1 and 5% by weight thereof on the area around the lips or on the lips of the members of a panel. An aqueous solution of an ingredient is considered to be bitter if the average bitterness evaluated by the panel is at least equal to that of 0.2 g of an aqueous solution of quinine at 8 µmol/l.

The bitterness of an aqueous solution of the ingredient can alternatively be evaluated by a panel of users. Each member of the panel does not have the same sensitivity to bitterness, but it must be reproducible. A sufficient number of reproducible members makes it possible to average the inter-individual disparities in such a way as to obtain a significant average evaluation, and an objective quantification of the bitterness. In order to judge the reproducibility of a member, said member is provided with several samples blind. Among these samples, two samples of the same composition are introduced. The evaluation of these two samples must be identical or substantially identical. For example, on a grading scale of 1 to 5, a difference in grade of 1 is tolerated.

The bitter organic ingredient is preferably hydrophilic. For the purpose of the invention, the term "hydrophilic compound" is intended to mean an organic compound which can be dissolved in the aqueous phase of a composition, or which can be dispersed therein in colloidal form or in micellar form.

This bitter cosmetic ingredient may have various cosmetic functions, for example a UV-screening agent or an active agent.

The hydrophilic bitter organic compound preferably comprises in its structure at least two rings, at least one of the two rings being aromatic. It is preferably substituted with at least one functional group chosen from the sulfonic acid group, the nitro group, the ketone function and the hydroxyl group.

According to one embodiment, the bitter organic ingredient comprises at least two aromatic rings.

The organic ingredient with a bitter taste is in particular a non-polymer compound chosen from the group consisting:
of compounds comprising a sulfonic acid function,
of compounds comprising at least two rings, including one aromatic ring, and a hydroxyl group,
of compounds comprising an —N—C=S or —N—C=O function, and
mixtures thereof.

The organic ingredient with a bitter taste is, for example, chosen from the group consisting of xanthines, such as such as caffeine, polyphenols, L-phenylalanine, urea, sucrose octaacetate, hesperidin, alpha-glucosyl hesperidin and hydrophilic organic UV-screening agents.

The organic ingredient with a bitter taste is, for example, a flavonoid, such as a flavanone, an isoflavone or a flavanol.

The organic ingredient with a bitter taste is, for example, present in the composition according to the invention in proportions ranging from 0.05 to 10% by weight relative to the total weight of the composition, preferably ranging from 0.1 to 8% by weight, and better still from 0.1 to 5% by weight relative to the total weight of the composition.

A hydrophilic organic UV-screening agent may be responsible for the bitterness experienced by the user when the latter accidentally applies the composition to the lips or the area around the lips.

The expression "hydrophilic organic UV-screening agent" is intended to mean any organic compound which absorbs ultraviolet (UV) radiation in the wavelengths range of from 280 nm to 400 nm and which can be dissolved in the aqueous phase of a composition, or which can be dispersed therein in colloidal form or in micellar form.

Among the hydrophilic UV-screening agents, use may be made of the following screening agents denoted below by their INCI name or their chemical name:
terephthalylidene dicamphorsulfonic acid (INCI name: terephthalylidene dicamphor sulfonic acid) sold under the name Mexoryl® SX by Chimex,
the bis-benzoazolyl derivatives as described in patents EP 669 323 and U.S. Pat. No. 2,463,264 and more particularly the compound disodium phenyl dibenzimidazole tetrasulfonate sold under the trade name Neo Heliopan® AP by Haarmann and Reimer,
p-aminobenzoic acid (INCI name: PABA) and derivatives thereof, such as 1-(4-aminobenzoate)-1,2,3-propanetriol (INCI name: Glyceryl PABA) and PEG-25 PABA sold under the name Uvinul® P25 by BASF,
2-phenylbenzimidazole-5-sulfonic acid (INCI name: phenylbenzimidazole sulfonic acid) sold in particular under the trade name Eusolex® 232 by Merck,
triethanolamine salicylate,
3-(4'-sulfobenzylidene)camphor (INCI name: benzylidene camphor sulfonic acid) sold under the name Mexoryl® SL by Chimex,
methylene bis-benzotriazolyl tetramethylbutylphenol (USAN name: bisoctrizole) sold under the reference Tinosorb® M, or MIXXIM® BB/100 by Fairmount Chemical;
3-(4'-trimethylammoniumbenzylidene)-1-bornan-2-one methyl sulfate (INCI name: camphor benzalkonium methosulfate) sold under the name "Mexoryl SO" by Chimex,
benzophenone-4 sold under the trade name "Uvinul MS40" by BASF, benzophenone-5, and benzophenone-9.

It is also possible to use, as hydrophilic organic UV-screening agent, organic UV-screening molecules which are lipophilic in nature (dissolved or dispersed in a nonaqueous liquid) which have been made hydrophilic by adsorption onto a hydrophilic support of small particle size, for instance polymer particles. Mention may, for example, be made of bisethylhexyloxyphenol methoxyphenyl triazine, which is a lipophilic UV-screening agent adsorbed onto particles of polymethyl methacrylate (PMMA). The hydrophilic organic UV-screening agent may therefore be a lipophilic organic UV-screening molecule adsorbed or absorbed onto a hydrophilic support, which may not screen out UV rays, such as an organic polymer.

The composition according to the invention comprises at least one steviol glucoside as sweetener.

The sweetener is advantageously incorporated in an amount sufficient to mask the bitterness of the organic ingredient with a bitter taste, without however destabilizing the composition or giving too sweet a taste that would become sickly. It is thus preferred for the amount of sweetener to be less than 1% by weight relative to the weight of the composition.

The first sweetening gustatory agent preferably represents from 0.05 to 2% by weight, more preferably from 0.1 to 1% by weight, preferentially from 0.2 to 0.6% by weight, more preferentially from 0.4 to 0.5% by weight, of the weight of the composition.

The sweetener is chosen from steviol glucosides and plant extracts containing same. The sweetener is, for example, chosen from stevioside, steviolbioside, rebaudiosides A, B, C, D and E, dulcosides A and B, and mixtures thereof. The sweetener is preferably rebaudioside A (sometimes called stevioside) or a plant extract containing rebaudioside A.

Rebaudioside A is a heteroside, the aglycone part of which, called steviol, is linked to two oside groups; one glucose unit and one glucose triholoside (IUPAC name: 19-O-beta-glucopyranosyl-13-O-(beta-glucopyranosyl(1-2)-beta-glucopyranosyl(1-3))-beta-glucopyranosyl-13-hydroxy-kaur-16-en-19-oic acid and CAS No. 58543-16-1). Its sweetening power is 250 to 450 times greater than that of sucrose.

Rebaudioside A can be advantageously extracted from Stevia, more precisely from its leaves. The species Stevia rebaudiana for example contains same. In the context of the invention, use may be made of an extract of Stevia rebaudiana, such as that sold under the reference Rebaten 97% Sweetener® by the company SEPPIC.

Plants of the Stevia genus grow naturally in Paraguay; they are also cultivated in South America and in Asia. In order to extract the rebaudioside A therefrom, the leaves of the plant are dried and reduced to powder, before undergoing aqueous extraction and then purification.

The composition according to the invention may comprise a second gustatory agent, chosen from sodium chloride, potassium chloride and zinc chloride, and mixtures thereof.

In one advantageous embodiment, it is preferred to use sodium chloride.

The concentration of the second gustatory agent preferably ranges from 0.0005 to 0.5%, more preferably from 0.01 to 0.3% by weight relative to the weight of the composition.

According to one embodiment, the composition comprises from 0.5 to 5% by weight, for example from 1 to 2.5% by weight, of benzophenone-4 relative to the weight of the composition. According to another embodiment, the composition comprises from 1 to 3% by weight of 2-phenylbenzimidazole-5-sulfonic acid relative to the weight of the composition. In these two embodiments, from 0.3 to 0.6% by weight, more preferably from 0.4 to 0.5% by weight of sweetener is preferably used. In these two embodiments, the sodium chloride advantageously represents from 0.2 to 0.3% by weight of the weight of the composition.

The composition of the invention preferably comprises odorous ingredients or perfuming plant extracts, for example a collection of ingredients of which the INCI name appearing on the listing of ingredients of the cosmetic product proposed for sale is "Fragrance". A fragrance is a compound or a mixture of compounds which is volatile at ambient temperature, the odour of which is detected. For the purpose of the invention, a fragrance is different from an aroma.

The term "fragrance" is intended to mean an odorous substance or a mixture of odorous substances which evaporate. Each fragrance has what is called a top note which is the odour that diffuses first when the fragrance is applied or when the container containing it is opened, a heart note or body which corresponds to the complete fragrance (emission for a few hours after the top note) and a base note which is the most persistent odour (emission for several hours after the heart note). The persistence of the base note corresponds to the persistence of the fragrance.

The term "fragrance" is intended to mean any organic compound capable of fragrancing the skin, the hair, the scalp, the lips or the nails.

In alcoholic products, the amount of fragrance will be more preferentially from 3 to 50% by weight, better still from 5 to 30%, even better still from 10 to 20% by weight relative to the total weight of the composition.

In care products, the amount of fragrance will preferentially be from 0.05 to 1% by weight, and better still from 0.3 to 0.7% by weight relative to the total weight of the composition. Perfumery raw materials, aromas and mixtures thereof may be used as fragrance. They may be, independently of one another, of natural or synthetic origin.

A perfumery raw materials and aromas of natural origin, mention may, for example, be made of extracts of flowers (lavender, rose, jasmine, ylang-ylang), of stems and of leaves (patchouli, geranium, petitgrain), of fruits (coriander, aniseed, cumin, juniper), of fruit peel (bergamot, lemon, orange), of roots (angelica, celery, cardamom, iris, rattan palm), of wood (pinewood, sandalwood, gaiac wood), of herbs and grasses (tarragon, lemongrass, sage, thyme), of needles and branches (spruce, fir, pine), of resins and of balms (galbanum, elemi, benjoin, myrrh, olibanum, opopanax).

As synthetic perfumery raw materials, mention may, for example, be made of benzyl acetate, benzyl benzoate, phenoxyethyl isobutyrate, p-tert-butylcyclohexyl acetate, citronellyl acetate, citronellyl formate, geranyl acetate, linalyl acetate, dimethylbenzylcarbinyl acetate, phenylethyl acetate, linalyl benzoate, benzyl formate, ethylmethylphenyl glycinate, alkylcyclohexyl propionate, styralyl propionate and benzyl salicylate, benzyl ethyl ether, linear alkanals containing from 8 to 18 carbon atoms, citral, citronellal, citronellyloxyacetaldehyde, cyclamenaldehyde, hydroxycitronellal, lilial and bourgeonal, ionones such as alpha-isomethylionone, and methyl cedryl ketone, anethole, citronellol, eugenol, isoeugenol, geraniol, linalol, phenylethyl alcohol, terpineol and terpenes. These compounds are often in the form of a mixture of two or more of these odorous substances.

Moreover, use may also be made of essential oils, components of aromas, for instance essences of sage, of camomile, of clover, of lemon balm, of mint, of cinnamon tree leaves, of lime tree blossom, of juniper, of vetiver, of olibanum, of galbanum, of labolanum and of lavandin.

Essence of bergamot, dihydromyrcenol, lilial, lyral, citronellol, phenylethyl alcohol, alpha-hexylcinnamaldehyde, geraniol, benzylacetone, cyclamenaldehyde, linalol, ambroxane, indol, hedione, sandelice, essences of lemon, of mandarin and of orange, allylamine glycolate, cyclovertal, essence of lavandin, essence of sage, beta-damascone, essence of geranium, cyclohexyl salicylate, phenylacetic acid, geranyl acetate, benzyl acetate and rose oxide are preferably used as perfumery raw materials, alone or as a mixture.

Among the known olfactory notes, mention may, for example, be made of hesperidium fragrances, aromatics, floral fragrances, musks, fruity fragrances, spices, oriental fragrances, marine fragrances, aquatic notes, chypre fragrances, woody fragrances, green fragrances and ferns, and mixtures thereof.

According to one embodiment, the olfactory note of the composition is floral, for example musk floral or green floral. The note of the fragrance may be aromatic musk floral or green rose floral.

The composition of the invention is intended to be applied to the face and is preferably in the form of an oil-in-water, or water-in-oil emulsion or of an aqueous gel. The composition is, for example, in the form of a facial care cream, of a face lotion, of a face serum or fluid, of a foundation, of a face milk, of a makeup-removing lotion, of a complexion base, or of a facial antisun product.

According to one preferred embodiment, the cosmetic or dermatological composition is not intended to be swallowed; its administration is topical and nonoral. The composition of the invention is not a food.

The subject of the invention is also the use of the combination of a first sweetening gustatory agent chosen from steviol glucosides, and of at least a second gustatory agent chosen from sodium chloride, potassium chloride and zinc chloride, and mixtures thereof, in a cosmetic composition intended to be applied to facial skin, containing a bitter compound, an aqueous phase and a fragrance, for suppressing the bitterness caused by the bitter compound without modifying the olfactory signature of the composition.

The lack of modification of the fragrance (which can also be expressed as the preservation of the olfactory signature) and the masking or the suppression of the bitterness of the bitter compound are advantageously permanent.

According to another of its aspects, the invention relates to a cosmetic process which consists in applying a composition as previously described to at least one part of the face, characterized in that, during the application of the product, the latter comes into contact with the lips, and in that the combination of said at least one steviol glucoside and of said chloride salt mask the bitterness of the bitter compound without distorting the olfactory note of the composition.

The characteristics previously described in relation to the composition of the invention are applicable alone or in combination with one another to the use and to the method according to the invention.

In the examples, all the percentages are given by weight, unless otherwise indicated, and the temperature is expressed in degrees Celsius unless otherwise indicated, and the pressure is atmospheric pressure, unless otherwise indicated.

Example 1

Care Creams

The following comparative compositions which contain sucralose as sweetener in combination with mint aroma were prepared.

| INCI name or chemical name | Comparative composition 1 | Comparative composition 2 | Comparative composition 3 |
|---|---|---|---|
| Water | | qs 100 | |
| Ethylhexyl methoxycinnamate | | 6.9 | |
| Dicaprylyl carbonate | | 4.3 | |
| Glycerin | | 4 | |
| Butylene glycol | | 3.7 | |
| Butyl methoxydibenzoylmethane | | 3 | |
| Polymethyl methacrylate | | 3 | |
| Cetearyl alcohol | | 2.8 | |
| Bis-ethylhexyloxyphenol methoxyphenyl triazine | | 2 | |
| Behenyl alcohol | | 1.7 | |
| Pentylene glycol | | 1.17 | |
| Octocrylene | | 1 | |
| Hydrophilic UV-screening agent: Benzophenone-4 | 1% | | |
| Hydrophilic UV-screening agent: PSA | | 2% | |
| Hydrophilic UV-screening agent: MBBT | | | 5% |
| Diglycerin | | 0.9 | |
| Steareth-21 | | 0.9 | |
| Silica | | 0.8 | |
| Phenoxyethanol | | 0.8 | |
| Decyloxazolidinone | | 0.8 | |
| Sodium acrylate copolymer | | 0.7 | |
| Cetearyl glucoside | | 0.7 | |
| Hydrogenated polyisobutene | | 0.6 | |
| Phenyl trimethicone | | 0.6 | |
| Sodium hydroxide | | 0.1 | |
| Fragrance | | qs | |
| Mixture | | 100% | |
| Addition to the above mixture of: | | | |
| Unipex ® mint aroma | | 0.01% by weight | |
| sucralose JKSS00 ® | | 0.45% by weight | |

PSA: Phenylbenzimidazole Sulfonic Acid
MBBT: Bis-benzotriazolyl tetramethylbutylphenol sold under the trade reference Tinosorb ® M, which is as a dispersion in a water/glycol mixture.

Gustatory and Olfactory Tests

The taste, the odour and the colour of compositions according to the invention containing a bitter hydrophilic organic UV-screening agent and gustatory agents were compared to the taste, to the odour and to the colour of reference compositions containing the same bitter hydrophilic UV-screening agent, but lacking gustatory agents. These reference tests are entitled Control 1, Control 2 and Control 3. Their composition corresponds to that of the mixture described in the previous table, containing neither mint aroma nor sucralose. The Control 3 composition contains 10% by weight of Tinosorb® M, i.e. 5% by dry weight of bis-benzotriazolyl tetramethylbutylphenol.

Make-Up of the Bitterness Panel

In order to grade the bitterness, volunteer participants were recruited for their experience in objective and descriptive characterization of sensory qualities and the ease with which they are able to disregard the hedonistic components.

They were coached regularly in order to verify their reproducibility. For this, they were asked to grade the bitterness of a proposed product from 1 to 5.
5=Zero
4=Weak
3=Medium
2=Strong
1=Very strong Each participant does not have the same sensitivity to bitterness, but must be reproducible in order to be part of the panel. A sufficient number of reproducible participants makes it possible to average the inter-individual disparities in such a way as to obtain a significant average, and an objective quantification of the bitterness.

In order to judge the reproducibility of a participant, said participant was proposed several samples blind. Among these samples two samples of the same composition were introduced. The evaluation of these two samples by each panellist should be identical. However, a difference of 1 was "tolerated" for one and the same sample.

Protocol for Sensory Analysis of Bitterness

Before beginning the grading of the bitterness, each panellist established the following conditions:

Not to have eaten or drunk anything for at least 2 hours before the test.

Not to have smoked for at least 2 hours before the test.
To be in the most olfactorily neutral atmosphere possible.
To avoid wearing fragranced cosmetics.
To have avoided foods that are too hot and can decrease the sensitivity of the taste buds.

Before beginning the analysis, each panellist rinsed their mouth with a little water.

Each panellist took 0.2 g of product and applied it to the area around the lips (the panellist simulated a generous application to the face that would spread over onto the lips). The panellist "tasted" the product and filled in the questionnaire.

Before proceeding with a new evaluation, the panellist rinsed their mouth with water and waited for a few minutes. The panellist then graded the intensity of the bitterness of this product in the mouth:
5=Zero
4=Weak
3=Medium
2=Strong
1=Very strong Make-Up of the Fragrance Panel The odour/fragrance panel was judged by olfactory experts.

Results

The results are presented in the three tables below.

| Sample evaluated | | Bitterness | Organoleptic criteria colour/odour/taste |
|---|---|---|---|
| Control 1 | Comparative | 1.86 | |
| Control 1 +0.225% NaCl | Comparative | 2.57 | Colour and odour comply compared with the control. |
| Control 1 +0.45% Rebaten 97% ® | Invention | 4 | Colour and odour comply compared with the control. Bitterness greatly reduced throughout |

-continued

| Sample evaluated | Bitterness | Organoleptic criteria colour/odour/taste |
|---|---|---|
| +0.225% NaCl | | the perception of the product in the mouth. |
| Control 1 +0.45% Rebaten 97% ® | Comparative | 3.0 Colour and odour comply compared with the control. The bitterness comes back after 10 seconds after alteration of the sweet taste. |

| Sample evaluated | Bitterness | Organoleptic criteria colour/odour/taste |
|---|---|---|
| Control 2 | Comparative | 2.14 |
| Control 2 +0.45% Rebaten 97% ® +0.225% NaCl | Invention | 2.42 Ok colour and odour. An acid effect was noted by several panellists - bitterness reduced throughout the perception of the product in the mouth. |
| Comparative composition 2 | Comparative | 4.7 OK colour Odour = slight minty effect - distortion of the weak olfactory note. |

| Sample evaluated | Bitterness | Organoleptic criteria colour/odour/taste |
|---|---|---|
| Control 3 | Comparative | 3.57 |
| Control 3 +0.45% Rebaten 97% ® +0.225% NaCl | Invention | 4.71 Ok colour and odour. Bitterness covered throughout the perception of the product in the mouth. |
| Comparative composition 3 | Comparative | 4.86 OK colour. Odour = slight minty effect - distortion of the weak olfactory note. Bitterness covered throughout the perception of the product in the mouth. |

Compositions 1 to 3 can be used in the cosmetics industry for application to the face and cause no displeasure when they accidentally come into contact with the lips and are capable of developing a bitterness associated with the presence of the hydrophilic organic UV-screening agent.

Example 2

Care Cream

The following composition was prepared.

| INCI name or chemical name | Composition 4 |
|---|---|
| Water | qs 100 |
| Ethylhexyl methoxycinnamate | 7.4 |
| Glycerin | 4.6 |
| Dicaprylyl carbonate | 4 |
| Butyl methoxydibenzoylmethane | 3 |
| Butylene glycol | 2.5 |
| Octocrylene | 2 |
| Pentylene glycol | 2 |
| Diglycerin | 1.9 |
| $C_{14}$-$C_{22}$ alcohols | 1.6 |

-continued

| INCI name or chemical name | Composition 4 |
|---|---|
| Polymethyl methacrylate | 1.5 |
| Silica | 1.5 |
| Hydrophilic UV-screening agent: Benzophenone-4 | 1.5 |
| Steareth-21 | 1 |
| Betaine | 1 |
| Phenoxyethanol | 0.8 |
| Phenyl trimethicone | 0.7 |
| Cocoglucoside | 0.6 |
| Rosa-hybrid flower extract | 0.5 |
| $C_{12}$-$C_{20}$ alkyl glucoside | 0.4 |
| Coconut alcohol | 0.4 |
| Polyacrylamide | 0.3 |
| $C_{13}$-$C_{14}$ isoparaffin | 0.2 |
| Sodium hydroxide | 0.2 |
| Fragrance | qs |
| Mixture | 100% |
| Addition to the above mixture of: | |
| Extract of Stevia rebaudiana (Rebaten 97 ®) | 0.45% by weight |
| NaCl | 0.225% by weight |

Sensory Analysis

A control composition (Control 4) corresponding to composition 4 was prepared by removing the stevia extract and the sodium chloride. The sensory analysis conditions were carried out according to the protocol of example 1. The results are given in the following table.

| Composition | Bitterness | Colour/odour |
|---|---|---|
| Comparative control 4 | 1.14 | |
| Composition 4 | 4 | Ok colour and odour. |
| Comparative control 4 +0.45% JKSS00 ® sucralose +0.01% Unipex ® mint aroma | 4.57 | OK colour. Odour = slight minty effect - distortion of the weak olfactory note. |

The care cream for application to the face gives no displeasure when it accidentally comes into contact with the lips and it is capable of developing a bitterness associated with the presence of benzophenone-4.

The invention claimed is:

1. A method for suppressing a bitterness of a cosmetic or dermatological composition without distorting an olfactory note thereof, said composition comprising an aqueous phase and being in a form of a product selected from the group consisting of a facial care cream, a face lotion, a face serum or fluid, a foundation, and a facial antisun product, said composition comprising a fragrance and "a hydrophilic organic ingredient with a bitter taste selected from the group consisting of xanthines, polyphenols, L-phenylalanine, urea, sucrose octaacetate, hesperidin, alpha-glucosyl hesperidin and a flavonoid that is dissolved in the aqueous phase," said method comprising adding to the aqueous phase of the composition a combination of from 0.05 to 2 weight % of at least one steviol glucoside and from 0.01 to 0.5 weight % of a chloride salt selected from the group consisting of sodium chloride, potassium chloride, zinc chloride and mixtures thereof so as to suppress the "bitter taste" of the hydrophilic organic ingredient without distorting an olfactory note of the composition.

2. The method of claim 1, wherein the hydrophilic organic ingredient with a bitter taste is not a hydrophilic organic UV-screening agent.

3. "The method of claim 1", wherein the flavonoid is selected from the group consisting of a flavanone, an isoflavone and a flavanol.

4. The method of claim 1, wherein the amount of the steviol glucoside is from 0.1 to 1 "weight %" of the cosmetic or dermatological composition.

5. The method of claim 1, wherein the amount of the hydrophilic organic ingredient with a bitter taste is from 0.1 to 5 "weight %" of the cosmetic or dermatological composition.

6. The method of claim 1, wherein the steviol glucoside is selected from the group consisting of rebaudioside A and plant extracts containing rebaudioside A.

7. The method of claim 1, wherein the steviol glucoside is an extract of Stevia.

8. The method of claim 7, wherein the steviol glucoside is a water-soluble extract of Stevia.

9. The method of claim 1, wherein the concentration of the chloride salt ranges from 0.01 to 0.3 "weight %" of the cosmetic or dermatological composition.

10. The method of claim 1, wherein the concentration of the steviol glucoside ranges from 0.2 to 0.6 "weight %" of the cosmetic or dermatological composition.

11. A method for suppressing a "bitter taste" of a cosmetic or dermatological composition without distorting an olfactory note thereof, said composition comprising an aqueous phase and being in a form of a product selected from the group consisting of a facial care cream, a face lotion, a face serum or fluid, a foundation, and a facial antisun product, said composition comprising a fragrance and a hydrophilic organic UV-screening agent with a bitter taste that is dissolved in the aqueous phase, selected from benzophenone-4, phenylbenzimidazole sulfonic acid and bis-benzotriazolyl tetramethylbutylphenol, said method comprising adding to the aqueous phase of the composition a combination of from 0.05 to 2 weight % of at least one steviol glucoside and from 0.01 to 0.5 weight % of a chloride salt selected from the group consisting of sodium chloride, potassium chloride, zinc chloride and mixtures thereof so as to suppress the bitterness of the hydrophilic organic ingredient without distorting an olfactory note of the composition.

12. "The method of claim 11", wherein the amount of fragrance is ranging from 0.05 to 1 "weight %" of the composition.

13. "The method of claim 11", wherein the amount of fragrance is ranging from 0.3 to 0.7 "weight %" of the composition.

\* \* \* \* \*